United States Patent [19]

Hope

[11] Plant 4,345

[45] Dec. 12, 1978

[54] KALANCHOE NAMED TABASCO

[75] Inventor: Claude Hope, Cartago, Costa Rica

[73] Assignee: Pan-American Plant Company, West Chicago, Ill.

[21] Appl. No.: 876,462

[22] Filed: Feb. 9, 1978

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler and Snow

[57] ABSTRACT

A cultivar of kalanchoe for greenhouse culture as a potted plant, suitable for year around flowering under photoperiod control and characterized by its intense orange-red flowers of medium size which exhibit minimal fading, its medium plant height with medium sized glossy foliage, its 10-week flowering response and its resistance to powdery mildew.

1 Drawing Figure

BACKGROUND OF THE NEW PLANT

My new variety of kalanchoe plant originated as a seedling of Melody (unpatented) × Red Empress (unpatented) effected by me in the course of my breeding efforts carried on at Cartago, Costa Rica, since 1969 with the object of producing new kalanchoe varieties suitable for commercial marketing. The attractive orange-red coloration of this plant excited me to reproduce the plant by means of cuttings and the success of that venture and subsequent propagation of the variety through successive generations with vegetative cuttings carried on by me at Cartago, Costa Rica, has shown that the novel characteristics of this variety hold true from generation to generation and appear to be firmly fixed.

Propagation of this new variety by vegetative cuttings is now being done at Cortez, Fla., U.S.A., and at West Chicago, Ill., U.S.A.

DESCRIPTION OF THE DRAWING

My new kalanchoe plant is illustrated by the accompanying photographic drawing which shows my new plant in full color, the showing being of a potted plant in full bloom and the color rendition being as nearly true as it is reasonably possible to obtain by conventional professional photographic procedures.

DESCRIPTION OF THE NEW PLANT

The following is a detailed description of my new variety of kalanchoe plant with the color designations according to the R.H.S. Colour Chart published by The Royal Horticultural Society of London, England.

THE PLANT

Origin: Seedling.
Parentage:
- *Seed parent.*—Melody (unpatented).
- *Pollen parent.*—Red Empress (unpatented).

Classification:
- *Botanic.*—*Kalanchoe blossfeldiana.*
- *Commercial.*—Kalanchoe pot plant.

Form: Bush.
Height: 20 to 26 cm.
Growth: Sturdy and very strong, upright and with medium vigor.
Branching: Normal, under natural conditions.
Foliage: Abundant.

- *Leaf size.*—Medium, about 8 to 12 cm. long and about 3.5 to 6.5 cm. wide.
- *Shape.*—Ovate with obtuse tip and sinuate margin.
- *Venation.*—Pinnate.
- *Texture.*—Thick, fleshy edge of leaf.
- *Surface aspect.*—Smooth and glossy.
- *Venation.*—Pinnate.
- *Color.*—Upper side — 147A. Under side — 147B.
- *Petioles.*—About 18 to 24 mm. long.

THE BUD

Shape: Generally cylindrical with a pointed tip before opening.
Size:
- *Diameter.*—About 2.0 to 2.5 mm.
- *Length.*—About 8 to 11 mm.

Rate of opening: Rapid; bud opens fully within 1 day.
Sepals: Number — four, surrounding the receptacle.
- *Appearance.*—Upstanding and spear-shaped.
- *Surface texture.*—Smooth.
- *Surface aspect.*—Shiny.
- *Color.*—Inside — 144A. Outside — 144A.

THE FLOWER

Flowering: 10-week response under photoperiod control. Can be flowered the year around.
- *Natural season flowering.*—November through January under Costa Rican conditions.

Blooms: Flower type — regular and complete.
- *Borne.*—Colymbose in form on a compound cyme.
- *Shape.*—Tubular; petals flat when first opened and reflexing as bloom matures.
- *Size.*—Medium. About 11 to 13 mm. in diameter and about 12 to 14 mm. in depth.
- *Petals.*—Number per flower — four. Form: Nearly oval, each separate and distinct. Size: About 7 mm. long and about 5 mm. wide. Texture: Firm. Appearance: Shiny. Color: Upper side — 44A with 14A at the base. Under side — 26D and 39B. Tonality of florescence at a distance of 8 ft.: 33A-B. Discoloration: Very little fade as bloom matures.

Peduncle: Sturdy and upright.
- *Surface texture.*—Smooth.
- *Color.*—146C.

Persistence: Flowers hang on and dry.
Effect of weather: None. This variety is recommended only for greenhouse culture.

Disease resistance: This plant has been observed to be resistant to powdery mildew in environments where that disease is present.

Fragrance: Typical kalanchoe.

Lasting quality: Approximately 4 weeks.

REPRODUCTIVE ORGANS

Stamens: Number — eight.

*Anthers.*—Color — Yellow.

*Filaments.*—Color — Yellow-Green.

*Pollen.*—Color — Yellow.

Pistils: Number — four.

*Stigmas.*—Color — Yellow-Green.

Ovaries: Four ovaries each developing multiple seeds.

This cultivar of kalanchoe is particularly distinguished by its intense orange-red flowers which exhibit minimal fading and are of medium size. The plant has an extended blooming period due to continuous flower bud development over several weeks and when in flower has an attractive plant height as a potted plant and a base cover of abundant glossy foliage.

I claim:

1. A new and distinctive cultivar of kalanchoe, substantially as herein shown and described, characterized by its upright growth displaying relatively large clusters of intense orange-red flowers of medium size and its base cover of relatively large glossy foliage.

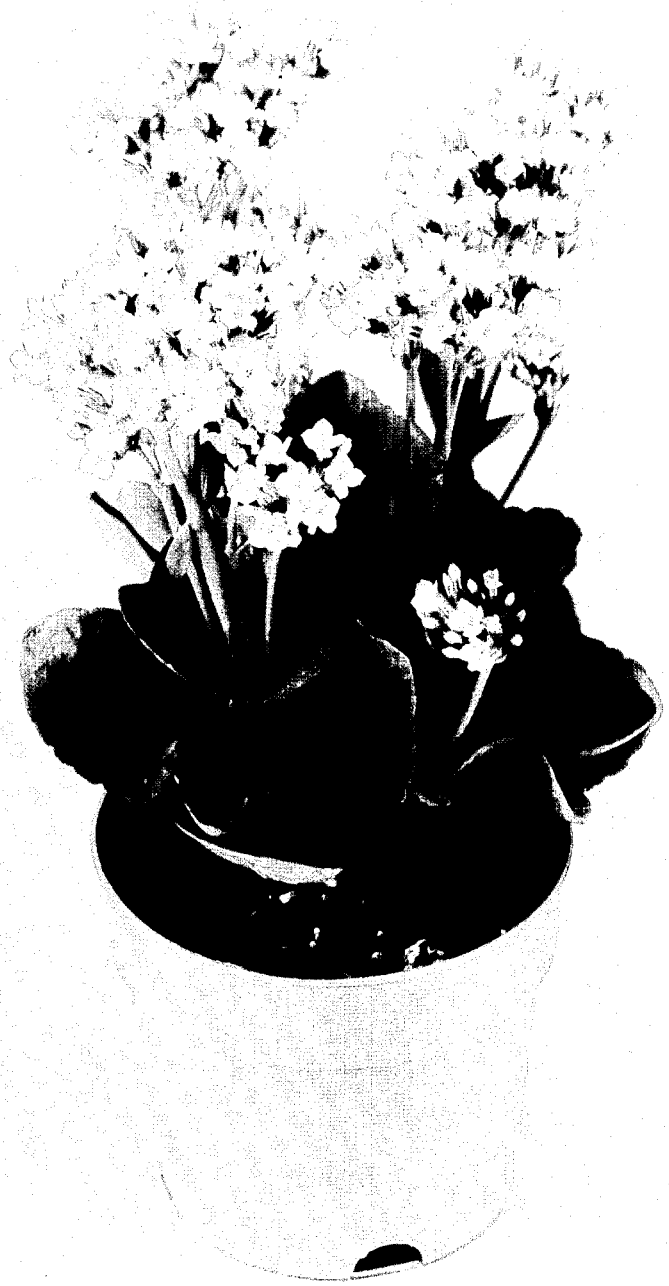

* * * * *